United States Patent
Iragavarapu-Charyulu et al.

(10) Patent No.: US 8,912,159 B2
(45) Date of Patent: Dec. 16, 2014

(54) ANALYZING SEMAPHORIN7A (SEMA7A) LEVELS FOR ASSESSING CANCER METASTATIC POTENTIAL AND METHODS OF TREATMENT

(71) Applicant: Florida Atlantic University, Boca Raton, FL (US)

(72) Inventors: Vijaya Iragavarapu-Charyulu, Boca Raton, FL (US); Ramon Garcia-Areas, Boca Raton, FL (US); Stephania Libreros, Boca Raton, FL (US)

(73) Assignees: National Institutes of Health (NIH), Washington, DC (US); U.S. Dept. of Health and Human Services (DHHS), Washington, DC (US); NIH Division of Extramural Inventions and Technology Resources (DEITR), Washington, DC (US)

( * ) Notice: Subject to any disclaimer, the term of this patent is extended or adjusted under 35 U.S.C. 154(b) by 0 days.

(21) Appl. No.: 13/775,793

(22) Filed: Feb. 25, 2013

(65) Prior Publication Data

US 2013/0225656 A1  Aug. 29, 2013

Related U.S. Application Data

(60) Provisional application No. 61/602,870, filed on Feb. 24, 2012.

(51) Int. Cl.
| | | |
|---|---|---|
| *C12N 15/113* | (2010.01) | |
| *G01N 33/68* | (2006.01) | |
| *C12Q 1/68* | (2006.01) | |
| *G01N 33/574* | (2006.01) | |
| *A61K 48/00* | (2006.01) | |

(52) U.S. Cl.
CPC ............ *G01N 33/6893* (2013.01); *A61K 48/00* (2013.01); *G01N 2800/52* (2013.01); *C12Q 1/6886* (2013.01); *C12Q 2600/158* (2013.01); *G01N 33/57415* (2013.01)
USPC ..................................................... 514/44 A

(58) Field of Classification Search
None
See application file for complete search history.

(56) References Cited

U.S. PATENT DOCUMENTS

| | | |
|---|---|---|
| 7,462,461 B2 | 12/2008 | Kikutani et al. |
| 2010/0285001 A1* | 11/2010 | Land et al. ................ 424/130.1 |

FOREIGN PATENT DOCUMENTS

| | | |
|---|---|---|
| WO | 2008024300 | 2/2008 |
| WO | 2013052631 | 4/2013 |

OTHER PUBLICATIONS

Capparuccia and Tamagnone, "Semaphorin signaling in cancer cells and in cells of the tumor microenvironment—two sides of a coin," Journal of Cell Science (2009) 122: 1723-1736.
Gan et al., "Role of semaphorin 7a signaling in transforming growth factor β1-induced lung fibrosis and scleroderma-related interstitial lung disease," Arthritis and Rheumatism (Aug. 2011) 63(8): 2484-2494.
Kang et al., "Semaphorin 7A plays a critical role in TGF-β-induced pulmonary fibrosis," Journal of Experimental Medicine (May 14, 2007) 204(5): 1083-1093.
Kim et al., "Disease-specific proteins from rheumatoid arthritis patients," J. Korean Med Sci (2006) 21: 478-484.

* cited by examiner

*Primary Examiner* — Tracy Vivlemore
(74) *Attorney, Agent, or Firm* — Amy A. Dobbelaere; Novak Druce Connolly Bove + Quigg LLP

(57) ABSTRACT

Methods, assays, and kits for determining a cancer's (e.g., breast cancer) metastatic potential and tumor aggressiveness in a subject (e.g., a human patient) and for measuring a subject's response to cancer therapy involve analyzing expression of Sema7A in a biological sample from the subject, and correlating increased expression of Sema7A in the biological sample compared to a control sample with metastatic potential of the cancer, wherein the expression of Sema7A is linearly proportional to the metastatic potential of the cancer in the subject. These methods, kits and assays provide for individualized diagnosis and treatment options for cancer (e.g., breast cancer) patients. They can be used independently, or can be combined with additional diagnostic tests and/or prognostic methods. Compositions, kits and methods for treating a subject having cancer (e.g., breast cancer) include administering a composition for inhibiting Sema7A expression or activity to the subject.

4 Claims, 10 Drawing Sheets

Representative of n=14

ANALYZING SEMAPHORIN7A (SEMA7A) LEVELS FOR ASSESSING CANCER METASTATIC POTENTIAL AND METHODS OF TREATMENT

CROSS-REFERENCE TO RELATED APPLICATIONS

This application claims the benefit of Provisional Application Ser. No. 61/602,870, filed Feb. 24, 2012, which is hereby incorporated by reference in its entirety, for all purposes, herein.

FEDERALLY SPONSORED RESEARCH

This invention was made with government support under grant nos. R15 CA135513-01 and R15 CA135513-01-OS awarded by the National Institutes of Health. The U.S. government has certain rights in the invention.

FIELD OF THE INVENTION

The invention relates generally to the fields of molecular genetics, molecular biology, and oncology.

BACKGROUND

In the United States, cancer is responsible for 25% of all deaths. Death from cancer is primarily due to metastasis of cancer cells to other organs followed by secondary tumor formation throughout the body. Breast cancer, for example, is the second-most common cause of cancer mortality among women with approximately 40,000 women and 480 men newly affected with this disease every year. Despite improved treatment options, breast cancer remains a devastating illness. There is a critical need for new predictive and diagnostic assays and treatments for breast and other solid tumor cancers.

SUMMARY

Described herein are methods, assays, and kits for determining a cancer's (e.g., breast cancer) metastatic potential and tumor aggressiveness in a subject (e.g., a human patient) and for measuring a subject's response to cancer (e.g., breast cancer) therapy, as well as compositions, kits and methods for inhibiting Sema7A expression or activity to treat a subject having cancer (e.g., breast cancer). It was discovered that the levels of Sema7A gene and its products in breast cancer tissue and breast cancer stem cells (CSCs) are proportional to the aggressiveness of the breast tumors, and that within the tumor tissue, the mesenchymal CSCs had the highest expression of Sema7A. It was also found that Sema7A is up-regulated in the tumor tissues of breast cancer patients but expression is minimal in the adjacent normal tissue. Additionally, implantation of breast tumor cell lines with altered Sema7A expression in BALB/c mice affected tumor growth, metastasis and survival. This diagnostic analysis serves as a method to determine the potential for breast cancer metastasis and tumor aggressiveness in individual patients from biopsy specimens. This method also serves as a useful tool to decide on proper management and treatment of this disease. These combined uses provide individualized diagnosis and treatment options for breast cancer patients. Sema7A may be useful as a novel therapeutic target to limit tumor growth and metastasis not only for breast cancer but for other solid tumors as well. The methods, assays and kits described herein can be used independently, or can be combined with additional diagnostic tests and/or prognostic methods.

Accordingly, described herein is an assay for determining metastatic potential of a breast cancer in a subject (e.g., a human). The assay includes analyzing expression of Sema7A in a biological sample from the subject; and correlating increased expression of Sema7A in the biological sample compared to a control sample with metastatic potential of the breast cancer. The expression of Sema7A is linearly proportional to the metastatic potential of the breast cancer in the subject. In the assay, the biological sample can be a needle biopsy sample, for example. Expression of Sema7A can be analyzed using polymerase chain reaction (PCR) and a pair of Sema7A-specific primers, using reverse-transcriptase PCR and a pair of Sema7A-specific primers, using a Sema7A-specific antibody and a protein assay, etc. The assay may further include analyzing expression of one or more breast cancer markers such as, for example, vimentin, osteopontin, MMP-3 and MMP-13. The breast cancer can be any type of breast cancer, including, for example, ER-negative breast cancer, ductal carcinomas, lobular carcinoma and male breast cancer. In one embodiment of the assay, cancer stem cells (CSCs) are isolated from the biological sample and analyzed for Sema7A expression, and expression of Sema7A in the CSCs is linearly proportional to the metastatic potential of the breast cancer in the subject.

Also described herein is a method for measuring a response to breast cancer therapy in a subject having breast cancer. The method includes: analyzing expression of Sema7A in a biological sample obtained from the subject at a first time point; analyzing expression of Sema7A in a biological sample obtained from the subject at a second time point, wherein the subject receives the breast cancer therapy simultaneously to or after the first time point and before the second time point; comparing the expression of Sema7A in the biological sample obtained from the subject at the first time point to the expression of Sema7A in the biological sample obtained from the subject at the second time point; and correlating decreased expression of Sema7A in the biological sample obtained from the subject at the second time point compared to the sample obtained from the subject at the first time point with a therapeutic response to the therapy. In the method, CSCs can be isolated from the biological sample and analyzed for Sema7A expression, and expression of Sema7A in the CSCs is linearly proportional to the metastatic potential of the breast cancer in the subject. In the method, therapy includes at least one of: anti-Sema7A antibodies, small weight molecular inhibitors and gene therapy. In one embodiment of the method, the sample obtained from the subject at the first and second time points is a needle biopsy sample.

Further described herein is a kit for determining metastatic potential of a breast cancer in a subject. The kit includes: at least one reagent for analyzing expression of Sema7A in a biological sample from the subject, wherein Sema7A and Sema7A expression products are markers for breast cancer metastatic potential; at least one control; and instructions for use. The at least one reagent can be, for example, a Sema7A-specific antibody, a pair of Sema7A-specific primers, etc.

Still further described herein is a composition including a therapeutically effective amount of a Sema7A inhibitor for inhibiting cancer cell growth in a subject having cancer cells and a pharmaceutically acceptable carrier. the Sema7A inhibitor can be, for example, a Sema7A-specific siRNA. In one embodiment, the cancer cells include breast cancer stem cells.

Additionally described herein is a method of inhibiting growth of breast cancer cells in a subject. The method includes administering to the subject a composition including a therapeutically effective amount for inhibiting cancer cell growth of a Sema7A inhibitor. In the method, administration of the composition to the subject results in death of breast cancer stem cells in the subject. In addition, administration of the composition to the subject decreases or prevents metastasis of the breast cancer cells. In one embodiment, the Sema7A inhibitor is an RNA molecule that reduces or prevents expression of Sema7A.

Unless otherwise defined, all technical terms used herein have the same meaning as commonly understood by one of ordinary skill in the art to which this invention belongs.

As used herein, "protein" and "polypeptide" are used synonymously to mean any peptide-linked chain of amino acids, regardless of length or post-translational modification, e.g., glycosylation or phosphorylation.

By the terms "Sema7A protein" or "Sema7A polypeptide" is meant an expression product of a Sema7A gene such as the native human Sema7A protein (accession no. CAJ55404.1; CAJ55403.1; CAJ55402.1; CAJ55401.1) or a protein that shares at least 65% (but preferably 75, 80, 85, 90, 95, 96, 97, 98, or 99%) amino acid sequence identity with the foregoing and displays a functional activity of a native Sema7A protein. Sema7A protein is also referred to as Semaphorin7A. A "functional activity" of a protein is any activity associated with the physiological function of the protein. For example, functional activities of a native Sema7A protein may include cell chemotaxis, cytoskeletal rearrangement and induction of extracellular matrix remodeling (inflammation).

As used herein, the phrases "Sema7A overexpression" and "overexpression of SEMA7A" are used interchangeably to mean increased levels of Sema7A mRNA and protein expression as compared to normal tissues.

By the term "gene" is meant a nucleic acid molecule that codes for a particular protein, or in certain cases, a functional or structural RNA molecule.

By the terms "Sema7A gene," "Sema7A polynucleotide," or "Sema7A nucleic acid" is meant a native human Sema7A-encoding nucleic acid sequence, e.g., the native human Sema7A gene (accession no. NG_011733.1); a nucleic acid having sequences from which a Sema7A cDNA can be transcribed; and/or allelic variants and homologs of the foregoing. Sema7A is also referred to as Semaphorin7A. The terms encompass double-stranded DNA, single-stranded DNA, and RNA.

As used herein, a "nucleic acid" or a "nucleic acid molecule" means a chain of two or more nucleotides such as RNA (ribonucleic acid) and DNA (deoxyribonucleic acid).

The terms "patient," "subject" and "individual" are used interchangeably herein, and mean a mammalian (e.g., human) subject to be treated, diagnosed, and/or to obtain a biological sample from.

As used herein, "bind," "binds," or "interacts with" means that one molecule recognizes and adheres to a particular second molecule in a sample or organism, but does not substantially recognize or adhere to other structurally unrelated molecules in the sample. Generally, a first molecule that "specifically binds" a second molecule has a binding affinity greater than about $10^8$ to $10^{12}$ moles/liter for that second molecule and involves precise "hand-in-a-glove" docking interactions that can be covalent and noncovalent (hydrogen bonding, hydrophobic, ionic, and van der waals).

The term "labeled," with regard to a cell, probe or antibody, is intended to encompass direct labeling of the cell, probe or antibody by coupling (i.e., physically linking) a detectable substance to the cell, probe or antibody.

When referring to a nucleic acid molecule or polypeptide, the term "native" refers to a naturally-occurring (e.g., a WT) nucleic acid or polypeptide.

As used herein, the terms "diagnostic," "diagnose" and "diagnosed" mean identifying the presence or nature of a pathologic condition.

The term "sample" is used herein in its broadest sense. A sample including polynucleotides, polypeptides, peptides, antibodies and the like may include a bodily fluid, a soluble fraction of a cell preparation or media in which cells were grown, genomic DNA, RNA or cDNA, a cell, a tissue, and the like. Examples of samples include saliva, serum, breast tissue, and blood. As used herein, the terms "treatment" and "therapy" are defined as the application or administration of a therapeutic agent to a patient, or application or administration of the therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease, or the predisposition toward disease.

As used herein, "sequence identity" means the percentage of identical subunits at corresponding positions in two sequences when the two sequences are aligned to maximize subunit matching, i.e., taking into account gaps and insertions. Sequence identity is present when a subunit position in both of the two sequences is occupied by the same nucleotide or amino acid, e.g., if a given position is occupied by an adenine in each of two DNA molecules, then the molecules are identical at that position. For example, if 7 positions in a sequence 10 nucleotides in length are identical to the corresponding positions in a second 10-nucleotide sequence, then the two sequences have 70% sequence identity. Sequence identity is typically measured using sequence analysis software (e.g., Sequence Analysis Software Package of the Genetics Computer Group, University of Wisconsin Biotechnology Center, 1710 University Avenue, Madison, Wis. 53705).

When referring to mutations in a nucleic acid molecule, "silent" changes are those that substitute one or more base pairs in the nucleotide sequence, but do not change the amino acid sequence of the polypeptide encoded by the sequence. "Conservative" changes are those in which at least one codon in the protein-coding region of the nucleic acid has been changed such that at least one amino acid of the polypeptide encoded by the nucleic acid sequence is substituted with another amino acid having similar characteristics.

Although kits, assays, and methods similar or equivalent to those described herein can be used in the practice or testing of the present invention, suitable kits, assays, and methods are described below. All publications, patent applications, and patents mentioned herein are incorporated by reference in their entirety. In the case of conflict, the present specification, including definitions, will control. The particular embodiments discussed below are illustrative only and not intended to be limiting.

DETAILED DESCRIPTION

Figure 1:
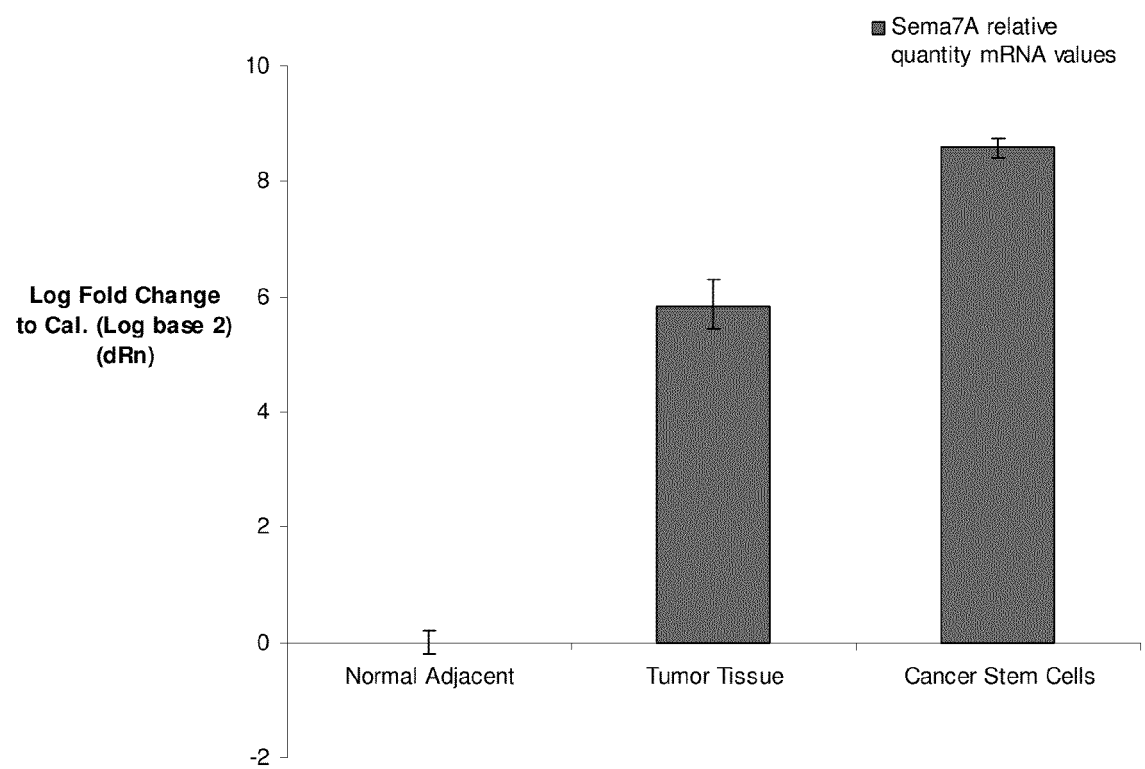
FIG. 1 is a graph showing Sema7A mRNA expression is increased in human breast tumor tissue and breast cancer stem cells. Graph represents n=7 patients.

Described herein are methods, assays and kits for determining breast cancer metastatic potential and tumor aggressiveness in an individual (e.g., a human patient). Also described herein are compositions, kits and methods for inhibiting Sema7A expression or activity to treat a subject having cancer (e.g., breast cancer). The methods, assays and kits for determining breast cancer metastatic potential and tumor aggressiveness in an individual can be performed with a very small number of breast cancer cells that are obtained from the patient using, for example, a biopsy specimen. In typical methods, assays and kits, the mRNA expression of Sema7A is measured by quantitative reverse transcriptase PCR (RT-PCR) of the cells using specific polymerase chain reaction (PCR) primers designed to quantitate the level of Sema7A mRNA, and the Sema7A protein levels are measured using specific antibodies against Sema7A (e.g., by quantitative western analysis, ELISA and in situ fluorescent monitoring of tumor cells and tissue as well as macrophages and T cells). These levels predict aggressiveness of breast cancer metastatic potential through comparison of Sema7A levels (determined by the methods described herein) against those established in previously characterized breast cancers of known metastatic potential as a reference. The feasibility of this approach has been demonstrated using human breast tissue samples and well established breast cancer cell lines, and the level of Sema7A was shown to be linearly proportional to breast cancer metastatic potential reflecting aggressiveness of the tumors. However, Sema7A may be useful as a novel therapeutic target to limit tumor growth and metastasis not only for breast cancer but for other solid tumors as well.

Biological Methods

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; The Condensed Protocols From Molecular Cloning: A Laboratory Manual, by Joseph Sambrook et al., Cold Spring Harbor Laboratory Press, Cold Spring Harbor, N.Y., 2006; and Current Protocols in Molecular Biology, ed. Ausubel et al., Greene Publishing and Wiley-Interscience, New York, 1995 (with periodic updates). Immunology techniques are generally known in the art and are described in detail in methodology treatises such as Advances in Immunology, volume 93, ed. Frederick W. Alt, Academic Press, Burlington, Mass., 2007; Making and Using Antibodies: A Practical Handbook, eds. Gary C. Howard and Matthew R. Kaser, CRC Press, Boca Raton, Fla., 2006; Medical Immunology, 6$^{th}$ ed., edited by Gabriel Virella, Informa Healthcare Press, London, England, 2007; and Harlow and Lane ANTIBODIES: A Laboratory Manual, Cold Spring Harbor Laboratory Press, Cold Spring Harbor, N.Y., 1988. The use of breast cancer cell lines is described herein. Known breast cancer cell lines are described, for example, in Neve et al., Cancer Cell 10:515-527, 2006. Conventional methods of gene transfer and gene therapy may also be adapted for use in the present invention. See, e.g., Gene Therapy: Principles and Applications, ed. T. Blackenstein, Springer Verlag, 1999; Gene Therapy Protocols (Methods in Molecular Medicine), ed. P. D. Robbins, Humana Press, 1997; Viral Vectors for Gene Therapy: Methods and Protocols, ed. Otto-Wilhelm Merten and Mohammed Al-Rubeai, Humana Press, 2011; and Nonviral Vectors for Gene Therapy: Methods and Protocols, ed. Mark A. Findeis, Humana Press, 2010.

Assays for Determining Metastatic Potential Of a Breast Cancer

Described herein are assays for determining metastatic potential of a breast cancer in a subject. Typically, an assay for determining metastatic potential of a breast cancer in a subject (e.g., mammals including humans, bovines, rodents, non-human primates, canines, etc.) includes: analyzing expression of Sema7A in a biological sample from the subject, and correlating increased expression of Sema7A in the biological sample compared to a control sample with metastatic potential of the breast cancer. In the assay, the expression of Sema7A is linearly proportional to the metastatic potential of the breast cancer in the subject. The biological sample can be any suitable sample from a subject. In a typical embodiment, the biological sample is a needle biopsy sample. Use of a needle biopsy sample may be particularly advantageous because in many instances, a needle biopsy will be obtained from a subject for other analyses, and/or as a matter of routine while visiting a physician for the analysis of a suspicious breast mass. However, other examples of suitable biological samples include other biopsy specimens, urine, blood, saliva, etc.

Because it was found that within the tumor tissue, the mesenchymal CSCs had the highest expression of Sema7A, the assays, methods and kits for determining metastatic potential of a breast cancer in a subject can include analyzing CSCs from a biological sample. In this embodiment, CSCs are isolated from the biological sample (e.g., a tumor biopsy specimen). CSCs are typically isolated by sorting CSCs using flow cytometry based on the surface expression of particular markers such as, for example, CD44, CD24 and EPCAM-1. Once isolated, the CSCs can be assessed for Sema7A expression. In the methods and assays described herein, expression of Sema7A in the CSCs is typically linearly proportional to the metastatic potential of the breast cancer in the subject. In a typical embodiment, the isolated CSCs are assessed in parallel with analysis of the tumor tissue obtained from the same biological sample.

In some embodiments, expression of Sema7A is analyzed using a Sema7A-specific antibody and a protein assay. Any suitable method or assay can be used to measure the level of Sema7A protein expression in the biological sample of a subject. Numerous antibody-based detection formats are well known in the art, and include ELISA (enzyme linked immunosorbent assay), radioimmunoassays, immunoblots, Western blots, flow cytometry, immunofluorescence assays, immunoprecipitation, protein A assays, immunoelectrophoresis assays, and other related techniques. In some embodiments, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the kits, assays and methods described herein. Antibodies specific for Sema7A may be provided in a diagnostic kit that incorporates at least one of these procedures to quantitate Sema7A expression. The kit may contain other components, packaging, instructions, or other material to aid the quantitation of the protein and use of the kit.

Anti-Sema7A antibodies as described herein can be obtained commercially or routinely made according to methods such as, but not limited to, inoculation of an appropriate animal with the polypeptide or an antigenic fragment, in vitro stimulation of lymphocyte populations, synthetic methods, hybridomas, and/or recombinant cells expressing nucleic acid encoding such anti-Sema7A antibodies. Immunization of an animal using purified recombinant Sema7A or peptide fragments thereof, is an example of a method of preparing anti-Sema7A antibodies. Similarly, immunization of an animal using purified recombinant Sema7A or peptide fragments thereof, is an example of a method of preparing anti-Sema7A antibodies.

In other embodiments, expression of Sema7A is analyzed at the DNA or mRNA level (or both). When analyzing Sema7A mRNA levels, RT-PCR and a pair of Sema7A-specific primers may be used. DNA and mRNA are prepared and analyzed according to well-established protocols. In some embodiments, in addition to or alternative to PCR, analysis of DNA can be carried out by amplification of the region of interest according to amplification protocols well known in the art (e.g., ligase chain reaction, strand displacement amplification, transcription-based amplification, self-sustained sequence replication (3SR), Qβ replicase protocols, nucleic acid sequence-based amplification (NASBA), repair chain reaction (RCR) and boomerang DNA amplification (BDA)). The amplification product can then be visualized directly in a gel by staining or the product can be detected by hybridization with a detectable probe. Also described herein are oligonucleotides for use as primers and/or probes for detecting and quantitating Sema7A levels according to the methods described herein.

Whether or not Sema7A is overexpressed in the biological sample can be determined by comparing the level of Sema7A expression in the biological sample to a baseline level (also known as a control level) of expression of Sema7A. A "baseline level" is a control level, and in some embodiments a normal level and/or a level not observed in subjects having metastatic or aggressive breast cancer. Therefore, it can be determined, based on the control or baseline level of Sema7A expression, whether a sample to be evaluated for metastatic or aggressive breast cancer has a measurable increase (i.e., overexpression, upregulation), decrease, or substantially no change in expression of Sema7A, as compared to the baseline level. In certain embodiments, the baseline level can be established from a previous sample from the subject being tested, so that the disease state of the subject can be monitored over time and/or so that the efficacy of a given therapeutic protocol can be evaluated over time.

In some embodiments of an assay for determining metastatic potential of a breast cancer in a subject, expression of one or more metastatic breast cancer markers in addition to Sema7A is analyzed. Examples of additional markers that can be analyzed include vimentin, osteopontin, MMP-3, MMP-13 and others. In embodiments in which expression of one or more markers in addition to Sema7A is analyzed, the combination of Sema7A and other biomarkers may provide a more reliable prediction of the metastatic potential of a breast cancer in a particular subject. In such an embodiment, the biological sample is contacted with at least one reagent that detects the expression of Sema7A and one or more reagents that detect the expression of the one or more markers in addition to Sema7A, respectively. The levels of expression of Sema7A and the one or more additional markers in the biological sample are measured, and overexpression of Sema7A is linearly correlated with the metastatic potential of the breast cancer in the subject. Depending on the particular one or more additional markers, their underexpression or overexpression may be correlated with the metastatic potential of the breast cancer in the subject.

Assays and Methods of Measuring a Response to Breast Cancer Therapy in a Subject In general, a method of monitoring treatment progress includes determining a level of diagnostic marker such as Sema7A or diagnostic measurement (e.g., screen, assay) in a subject suffering from or susceptible to a disorder or symptoms thereof associated with breast cancer in which the subject has been administered a therapeutic composition for the treatment of breast cancer. The level of marker determined in the method can be compared to known levels of marker in either healthy normal controls or in other afflicted patients, or in previously characterized breast cancer cell lines or tumors to establish the subject's disease status. In preferred embodiments, a second level of marker (e.g., Sema7A) in the subject is determined at a time point later than the determination of the first level, and the two levels are compared to monitor the course of disease or the efficacy of the therapy. In certain preferred embodiments, a pre-treatment level of marker in the subject is determined prior to beginning treatment according to the methods described herein; this pre-treatment level of marker can then be compared to the level of marker in the subject after the treatment commences, to determine the efficacy of the treatment.

Assays and methods for measuring a response (e.g., monitoring treatment progress) to breast cancer therapy in a subject having breast cancer typically include: analyzing expression of Sema7A in a biological sample obtained from the subject at a first time point; analyzing expression of Sema7A in a biological sample obtained from the subject at a second time point (wherein the subject receives the breast cancer therapy simultaneous to or after the first time point and before the second time point); comparing the expression of Sema7A in the biological sample obtained from the subject at the first time point to the expression of Sema7A in the biological sample obtained from the subject at the second time point;

and correlating decreased expression of Sema7A in the biological sample obtained from the subject at the second time point compared to the sample obtained from the subject at the first time point with a therapeutic response to the therapy.

As described above, any suitable sample (biological sample) can be analyzed. For example, the sample obtained from the subject at the first and second time points is a needle biopsy sample. Typically, the subject is a mammal such as a human. In some embodiments, samples from a plurality (e.g., 2, 3, 4, 5, 10, 15, 20, 25, 30, 35, 40, 50, 100, etc.) of subjects who have breast cancer are analyzed. Any suitable reagent for detecting Sema7A expression can be used. In one embodiment, a Sema7A-specific antibody (e.g., monoclonal, polyclonal, Fab fragment, etc.) is used. In some embodiments, a method involving Sema7A-specific PCR can be used to measure a response (e.g., monitor treatment progress) to breast cancer therapy in a subject. In addition to the first and second time points, expression of Sema7A can be analyzed in biological samples taken from the subject at other time points, e.g., third, fourth, fifth, sixth time points, etc. For example, if multiple courses of therapy are administered to the subject, expression of Sema7A can be analyzed in biological samples taken from the subject after each course of therapy. To measure a response to a particular therapy, a measurement(s) may be taken at any suitable time (e.g., at the time of diagnosis).

Assays for Determining Metastatic Potential of Additional Cancers and for Measuring Responses to Therapies of Additional Cancers Although the experiments described herein pertain to breast cancer, the methods, assays and kits can be used for determining metastatic potential of cancers other than breast cancers, and for measuring a response to a therapy for a cancer other than breast cancer. As used herein, "cancer" refers to all types of cancer or neoplasm, benign or malignant tumors found in mammals, including, but not limited to: leukemias, lymphomas, melanomas, carcinomas and sarcomas. Examples of cancers are cancer of the brain, breast, pancreas, cervix, colon, head and neck, kidney, lung, non-small cell lung, melanoma, mesothelioma, ovary, sarcoma, stomach, prostate, testicles, uterus and medulloblastoma. Additional cancers for which metastatic potential can be determined using the methods, assays and kits described herein include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

Kits

Described herein are kits for determining a cancer's (e.g., breast cancer) metastatic potential and tumor aggressiveness in an individual (e.g., a human patient). A typical kit includes at least one reagent for detecting the level of Sema7A expression (e.g., detecting Sema7A DNA and mRNA levels, detecting Sema7A protein levels) in a biological sample (e.g., a biological sample obtained by a needle biopsy) from the subject, at least one control, and instructions for use. In one embodiment, a kit includes a monoclonal or polyclonal antibody to Sema7A, a detectable label, and instructions for use. In another embodiment, the kit includes Sema7A-specific primers for PCR, e.g., PCR and RT-PCR, and instructions for use. The controls for RNA and DNA can be housekeeping genes such as, for example, b-Actin or GAPDH. For protein determination using ELISA kits—all the components necessary are contained in the kit. The controls for these are typically samples from non-tumor tissue. Such kits can also be used, for example, to measure a subject's response to breast cancer therapy.

Compositions and Methods for Inhibiting Cancer Cell Growth

Compositions described herein for inhibiting cancer cell growth include a therapeutically effective amount of an inhibitor of Sema7A expression for inhibiting cancer (e.g., aggressive breast cancer) cell growth and a pharmaceutically acceptable carrier. Inhibiting cancer cell growth includes inducing death (killing of) of the cancer cells, reducing or blocking metastasis, and/or inducing differentiation of the cancer cells (promoting a more differentiated phenotype). Any suitable inhibitor of Sema7A activity or expression can be used, e.g., anti-Sema7A antibody, small molecular weight inhibitor, nucleic acid, etc. Such compositions can be used to inhibit growth of any type of cancer cell that overexpresses Sema7A. In addition to breast cancer, examples of cancers that can be inhibited using the compositions include prostate, colon, glioblastoma, pancreatic, and lung tumors.

An inhibitor of Sema7A reduces the level of Sema7A in a cell and/or reduces the activity of Sema7A in a cell. Any agent that reduces the level of Sema7A in a cell and/or reduces the activity of Sema7A in a cell can be used. An inhibitor of Sema7A to reduce the level of Sema7A protein in the cell may be an inhibitor of transcription and/or translation of Sema7A. In addition, an inhibitor of Sema7A to reduce the level of Sema7A protein in the cell may stimulate degradation of the Sema7A protein and/or Sema7A-encoding RNA. An inhibitor of Sema7A expression may be a nucleic acid, a chemical compound (e.g., a drug), a polypeptide, a peptide, etc. Small molecule inhibitors that inhibit Sema7A activity by altering its protein conformation or by interfering with essential protein-protein interactions may be used. Alternatively, an inhibitor of Sema7A transcription and/or translation may be a nucleic acid-based inhibitor such as an antisense oligonucleotide complementary to a target Sema7A mRNA, as well as ribozymes and DNA enzymes which are catalytically active to cleave the target mRNA. Therapeutic nucleic acid molecules as described herein may be in the form of RNA (e.g., mRNA, microRNA, siRNA, shRNA or synthetic chemically modified RNA) or in the form of DNA (e.g., cDNA, genomic DNA, and synthetic DNA). The DNA may be double-stranded or single-stranded, and if single-stranded, may be the coding (sense) strand or non-coding (anti-sense) strand. In the experiments described herein, administration of shRNA against Sema7A was shown to reduce tumor cell growth in mammals (Example 1), and thus in one embodiment, a composition for treating breast cancer by inhibiting cancer cell growth and/or metastasis in a subject includes a therapeutically effective amount of shRNA against Sema7A delivered as an oligonucleotide or within a viral vector or nanoparticle and a pharmaceutically acceptable carrier.

Many vectors useful for introducing exogenous nucleic acids into target mammalian cells are available. The vectors may be episomal, e.g. plasmids, virus derived vectors such cytomegalovirus, adenovirus, adeno-associated virus (AAV), lentivirus etc., or may be integrated into the target cell genome, through homologous recombination or random integration, e.g. retrovirus derived vectors such MMLV, HIV-1, ALV, etc. In one embodiment, the inhibitor of Sema7A expression is a nucleic acid contained within a viral vector. In such an embodiment, recombinant virions (particles) containing the viral vector are administered to the subject. Viruses are naturally evolved vehicles which efficiently deliver their genes into host cells and therefore are desirable vector systems for the delivery of therapeutic nucleic acids. Preferred viral vectors exhibit low toxicity to the host cell and produce/deliver therapeutic quantities of the nucleic acid of interest (in some embodiments, in a tissue-specific manner). Retrovirus-based vectors, Lentivirus vectors, adenovirus based vectors, and AAV-based vectors are examples of viral vectors that may be used. Such recombinant virions may be pseudotyped.

Methods of inhibiting growth of breast cancer cells in a subject include administering to the subject a composition including a therapeutically effective amount of a Sema7A inhibitor for inhibiting breast cancer cell growth. In some embodiments, administration of the composition to the subject results in death of cancer stem cells (e.g., breast cancer stem cells), and/or prevention of metastasis of cancer stem cells. Any suitable methods of administering such a composition to a subject may be used. In these methods, the compositions can be administered to a subject by any suitable route, e.g., systemically by intravenous injection, directly to a target site, parenterally, orally, etc. The compositions may be administered directly to a target site by, for example, surgical delivery to an internal or external target site, or by catheter to a site accessible by a blood vessel. For example, in a method of inhibiting growth of breast cancer cells in a subject and treating breast cancer in the subject, a composition as described herein may be delivered by intravenous injection. The compositions may be administered in a single bolus, multiple injections, or by continuous infusion (e.g., intravenously, by peritoneal dialysis, pump infusion). For parenteral administration, the compositions are preferably formulated in a sterilized pyrogen-free form. As indicated above, the compositions described herein may be in a form suitable for sterile injection. To prepare such a composition, the suitable active therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like. The compositions described herein may be administered to mammals (e.g., rodents, humans, nonhuman primates, canines, felines, ovines, bovines) in any suitable formulation according to conventional pharmaceutical practice (see, e.g., Remington: The Science and Practice of Pharmacy (20th ed.), ed. A. R. Gennaro, Lippincott Williams & Wilkins, (2000) and Encyclopedia of Pharmaceutical Technology, eds. J. Swarbrick and J. C. Boylan, Marcel Dekker, New York (1988-1999), a standard text in this field, and in USP/NF). A description of exemplary pharmaceutically acceptable carriers and diluents, as well as pharmaceutical formulations, can be found in Remington: supra. Other substances may be added to the compositions to stabilize and/or preserve the compositions.

The therapeutic methods described herein in general include administration of a therapeutically effective amount of the compositions described herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider. The methods and compositions herein may be also used in the treatment of any other disorders in which overexpression of Sema7A may be implicated.

Effective Doses

The compositions described herein are preferably administered to a mammal (e.g., human) in an effective amount, that is, an amount capable of producing a desirable result in a treated mammal (e.g., treating breast cancer). Such a therapeutically effective amount can be determined according to standard methods. Toxicity and therapeutic efficacy of the compositions utilized in methods of the invention can be determined by standard pharmaceutical procedures. As is well known in the medical and veterinary arts, dosage for any one subject depends on many factors, including the subject's size, body surface area, age, the particular composition to be administered, time and route of administration, general health, and other drugs being administered concurrently. A delivery dose of a composition as described herein is determined based on preclinical efficacy and safety.

Data and Analysis

Use of the assays, methods, and kits described herein may employ conventional biology methods, software and systems. Useful computer software products typically include computer readable medium having computer-executable instructions for performing logic steps of a method. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001). See U.S. Pat. No. 6,420,108.

The assays, methods, and kits described herein may also make use of various computer program products and software for a variety of purposes, such as reagent design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170. Additionally, the embodiments described herein include methods for providing data (e.g., experimental results, analyses) and other types of information over networks such as the Internet.

EXAMPLES

The present invention is further illustrated by the following specific examples. The examples are provided for illustration only and should not be construed as limiting the scope of the invention in any way.

Example 1

Exploring the Novel Role of Semaphorin7A in Breast Cancer

Reactivation of embryogenesis related processes, such as neurogenesis, is a powerful mechanism used by tumor cells to enhance their survival and propagation. Recent studies have shown that many types of solid tumors express neurogenic molecules independent of the tumor's geography. Semaphorins are a compelling example of these pleiotropic neuronal molecules. Semaphorins were originally characterized for their role in axonal guidance and to date 8 different classes have been identified. Class 3, 4, 5 and 6 Semaphorins have been found to play a role in cancer and other inflammatory diseases. Semaphorin7A (Sema7A), has not yet been studied in the context of cancer. It has however been associated with fibrosis, inflammation and immune modulation. Most Semaphorins are repellent cues and inhibit cellular migration, but Sema7A is the only vertebrate Semaphorin that serves as an axon chemoattractant. Sema7A also promotes dendricity, adhesion and motility during neuronal development, monocyte differentiation and osteoclast development. All these cellular properties have been attributed to Sema7A's ability to activate p38 mitogen-activated protein kinase pathway (MAP-kinase) through $\alpha1\beta1$ integrins. We have recently discovered that Sema7A is over-expressed in the tumor tissue of breast cancer patients compared to the adjacent normal tissue. Within the tumor tissue, the mesenchymal cancer stem cells had the highest expression of Sema7A Sema7A. We have also found that breast cancer cell lines of a mesenchymal phenotype express high levels of Sema7A and that Transforming growth factor beta-1 can induce Sema7A expression in breast epithelial cells.

This proposal aims to unravel the functional role of Sema7A in breast cancer progression. We hypothesize that Sema7A expression in tumor cells may lead to increased tumor cell dendricity, migration, and adhesion through the activation of the MAP-kinase pathway and mediating epithelial to mesenchymal transition (EMT). Similar to its role in neurogenesis, in the tumor microenvironment Sema7A could contribute to tumor cell migration and tissue remodeling. Therefore, Sema7A could prove to be a novel therapeutic target to limit tumor growth and metastasis not only for breast cancer but for other solid tumors as well. The proposed project will test if Sema7A expression can be correlated with disease severity and be established as a tumor marker and therapeutic target.

Specific Aims

While studying the role of the immune system in breast cancer and the inflammatory response, we discovered that an axonal guidance molecule Semaphorin 7A (Sema7A) is expressed by both tumor cells and the immune cells of mammary tumor bearing mice. We then confirmed that Sema7A is up-regulated in the tumor tissues of breast cancer patients but expression is minimal in the adjacent normal tissue. We also found that TGF-$\beta_1$ is a potent inducer of Sema7A in breast cell lines. Currently, Sema7A has not been studied in the context of any type of cancer, therefore study of this molecule in breast cancer patients and in mouse models of breast cancer will contribute to understanding the role of this molecule in cancer progression and metastasis. We hypothesize that Sema7A may have a novel functional role in breast cancer as an inducer of the epithelial to mesenchymal transition and cell chemoattractant.

To correlate Sema7A expression with disease in breast cancer patients, we will: establish soluble Sema7A serum levels in breast cancer patients and breast cancer free control subjects; determine Sema7A expression in peripheral blood leukocytes from breast cancer patients and breast cancer free control subjects; and determine Sema7A expression in breast tumor tissue, breast cancer stem cells and normal adjacent tissue of breast cancer patients. To elucidate the mechanisms involved in Sema7A induction and the downstream effects of Sema7A on metastatic potential, we will: assess which pathway(s) play a role in the TGF-$\beta_1$ induction of Sema7A in breast cell lines; determine if differential production of Sema7A affects the expression of epithelial and mesenchymal markers, as well as metastasis-related MMPs; and determine if Sema7A affects the morphology and invasive potential of breast epithelial cells. To assess the role of tumor-derived Sema7A on mammary tumor growth, we will: determine the in vivo effect of silencing Sema7A in 4T1 cells on tumorigenesis; determine the in vivo effect of over-expressing Sema7A in 4T1 cells on tumorigenesis; and assess if tumor derived Sema7A affects leukocyte infiltration, neovascularization and cell survival/proliferation.

The results of these studies may be translated into the development of new therapeutic strategies for an effective response against breast cancers and other solid tumors. Using gene arrays, we discovered that Sema7A regulates the genes involved in and epithelial to mesenchymal transition, tumor cell invasion and tumor cell migration No published studies to date have investigated the role Sema7A in any type of cancer. We are the first to discover that Sema7A plays a role in cancer (breast cancer).

Background

Both mesenchymal and epithelial cells play an important role during embryogenesis. Developmental cells have the ability to transform from epithelial to mesenchymal. This switch is called the EMT, and the reverse being Mesenchymal to Epithelial Transition (MET). Some of the transcription factors that regulate these transitions include Snail and Slug, Twist, Six1, and Cripto and the related signaling pathways include the TGF-beta, PI3K/AKT and Wnt/beta-catenin pathway (Micalizzi, et al., J Mammary Gland Biol Neoplasia, 2010. 15(2): p. 117-34.). During breast cancer development, there is an enhanced EMT in the breast epithelia and it is tightly correlated with poor prognosis. Mesenchymal breast cells have increased ability to disseminate from the primary tumor, survive in circulation and establish micrometastasis. It has been shown that EMT increases microtentacle formation in breast cells and that these structures increase the tumor cell's ability to disseminate from the primary tumor (Whipple, R. A., et al., Cancer Res, 2010. 70(20): p. 8127-37.). There is also an emerging relationship between EMT and breast cancer stem cells (BCSC). BCSC have more of a mesenchymal phenotype and have an increased malignant potential (Micalizzi, et al., J Mammary Gland Biol Neoplasia, 2010. 15(2): p. 117-34.). There is strong evidence that embryonic pathways can give tumor cells certain stem cell characteristics, such as self-renewal and multi-potency.

Semaphorins are a family of proteins that were established as repellent cues in axonal guidance and synapse formation during development (Kolodkin, et al., Cell, 1993. 75(7): p. 1389-99.). It is now known that they not only exert a repulsive effect in axonal guidance but they can also be attractive axonal cues. Currently there are a total of twenty known types of Semaphorins that have been discovered in invertebrates, vertebrates and viruses. The Semaphorin family is divided into eight classes. All Semaphorins share a conserved Sema domain in the N terminus and range in size of from 400 to 1,000 amino acids, and most dimerize to become functional (Zhou, et al., Trends Biochem Sci, 2008. 33(4): p. 161-70.). Variations in C-terminal motifs are the key differentiation factor among Semaphorins (Zhou, et al., Trends Biochem Sci, 2008. 33(4): p. 161-70.). Sema7A is the only Semaphorin in the class VII family and is the only Semaphorin that is GPI-anchored (Xu, X., et al., J Biol Chem, 1998. 273(35): p. 22428-34.). It is an 80 kDa membrane protein and can be cleaved off the membrane by ADAM-17 (Fong, K. P., et al., Blood, 2011. 117(1): p. e15-26.). Sema7A was originally identified as the vertebrate homologue of virally encoded Semaphorins A39R and AHV. Like the viral Semaphorins, Sema7A binds a virus encoded Semaphorin protein receptor (VESPR) that is also known as Plexin C1. This receptor is expressed by dendritic cells, monocytes and neutrophils. Unlike the A39R Semaphorin, the induction of Sema7A on monocyte chemotaxis and activation were not found to be mediated through the receptor Plexin C1. The effects following the binding of Plexin C1 and Sema7A are largely unknown. It is now known that the immune modulatory effects of Sema7A are mediated through the very late antigen 1 dimer, $\alpha1\beta1$ integrin. This finding departs from the traditional notion that Semaphorins signal through plexins and neuropillins. After binding $\alpha1\beta1$ integrin, Sema7A induces phosphorylation of focal adhesion kinase and MAP kinase. In human studies, Sema7A has been shown to be involved in chronic inflammatory diseases like chronic obstructive pulmonary disease (COPD) and rheumatoid arthritis. However, no studies have correlated Sema7A with more severe inflammatory diseases such as cancer.

Sema7A promotes dendricity not only in axons, but also in melanocytes, osteoclasts and monocytes. It was shown that interactions between Sema7A and $\alpha1\beta1$ integrins lead to cytoskeleton rearrangements and dendrite formation through MAPkinase activation in osteoclast differentiation and human melanocytes (Pasterkamp, R. J., et al., Nature, 2003. 424(6947): p. 398-405.; Delorme, G., et al., Biol Cell, 2005. 97(7): p. 589-97.; Scott, G. A. et al., J Invest Dermatol, 2008. 128(1): p. 151-61.). Sema7A is also an important regulator of tissue remodeling by inducing fibrosis (Kang, H. R., et al., J Exp Med, 2007. 204(5): p. 1083-93.; Kopp, M. A., et al., Glia, 2010. 58(14): p. 1748-56.). A pulmonary fibrosis study showed that expression of Sema7A and its receptors, Plexin C1 and $\alpha1\beta1$ integrins are induced by TGF-$\beta_1$ and that Sema7A contributes to TGF-$\beta_1$-derived fibrosis and tissue remodeling (Kang, H. R., et al., J Exp Med, 2007. 204(5): p. 1083-93.). It was found that that TGF-$\beta_1$ induction of Sema7A in the murine fibrotic lung was mediated by the PI3K/AKT pathway. Similarly, recent studies found Sema7A (+) astrocytes and Sema7A accumulation in fibrotic tissue following spinal cord injury via activation the PI3K/AKT pathway (Kopp, M. A., et al., Glia, 2010. 58(14): p. 1748-56.). The PI3K/AKT pathway has been found to play an important role in mediating TGF-$\beta_1$ pro-tumorigenic effects like promoting the epithelial to mesenchymal transition. Although the epithelial to mesenchymal transition (EMT) promotes cell dendricity and contributes to fibrosis, no studies to date have directly correlated EMT and Sema7A.

Sema7A illustrates the involvement of Semaphorins in regulating innate immune cells. Sema7A is expressed by lymphoid and myeloid cells. In the immune system, Sema7A is expressed by activated T lymphocytes and monocytes. Sema7A was found to induce the production proinflammatory cytokines through the $\alpha1\beta1$ integrin in both monocytes (Holmes, S., et al., Scand J Immunol, 2002. 56(3): p. 270-5.) and T cells (Suzuki, K., et al., Nature, 2007. 446(7136): p. 680-4.). As a GPI-anchored protein, Sema7A is recruited to lipid rafts that accumulate at the immunological synapse between T cells and macrophages and interacts with $\alpha1\beta1$ integrin to activate the MAP kinase pathway. Direct immunization of Sema7A-deficient mice and adoptive transfer of antigen-specific Sema7A-deficient T cells do not induce T-cell-mediated immune responses like contact hypersensitivity (Suzuki, K., et al., Nature, 2007. 446(7136): p. 680-4.). Sema7A-knockout mice resist the development of inflammation after hapten-induced contact hypersensitivity (Okuno, T. et al., FEBS Lett, 2011.).

Preliminary Data

To establish clinical relevancy, we first determined if Sema7A and Plexin C1 are expressed in tumor tissues of breast cancer patients compared to the corresponding normal tissue. Breast tissue samples were collected from untreated female patients (43 to 49 years) undergoing a double mastectomy and then submitted for pathological analysis. Cancer stem cells (CD133+/CD44+/CD29+) were isolated from tumor tissues by FACS. RNA was extracted and used to produce cDNA by conventional RT-PCR followed by real time PCR to assay gene expression profiles. We found that Sema7A mRNA expression was shown to be increased in human breast tumor tissue and breast cancer stem cells. In this experiment, breast tissues were collected from untreated breast cancer patients (43 to 49 years) when undergoing a double mastectomy and then submitted for pathological analysis. Cancer stem cells (CD44+/CD24−) were isolated from tumor tissues by FACS. RNA was extracted and used to make cDNA by conventional RT-PCR to then assay gene expression by real time PCR. Graph represents n=7 patients. The results are shown in FIG. 1.

We then wanted to establish an in vitro system to study the functional role of Sema7A in the breast epithelia. To do so, we assayed the Sema7A expression in human breast cell lines with varying degrees of malignancy using quantitative real-time PCR (qRT-PCR). The very aggressive MDA-231 cells had significantly higher levels of Sema7A compared to less aggressive MD-468, non-metastatic MCF-7 and the benign MCF-10A cells.

Multiple reports have found that Sema7A is strongly induced by TGF-$\beta_1$, therefore we tested if TGF-$\beta_1$ would induce Sema7A in a mammary cell line with minimal Sema7A expression. We treated MCF-10A cells with 5 ng/ml of TGF-$\beta_1$ or vehicle for 18, 24 or 36 hours. MCF-10A cells were then assayed for Sema7A gene expression by qRT-PCR. We found that within 18 hours, TGF-$\beta_1$ significantly increased the expression of Sema7A in MCF-10A cells. TGF-$\beta_1$ is a key inducer of epithelial to mesenchymal transition (EMT) and Sema7A could serve as a down-stream effecter of TGF-$\beta_1$ in EMT.

Figure 2A:
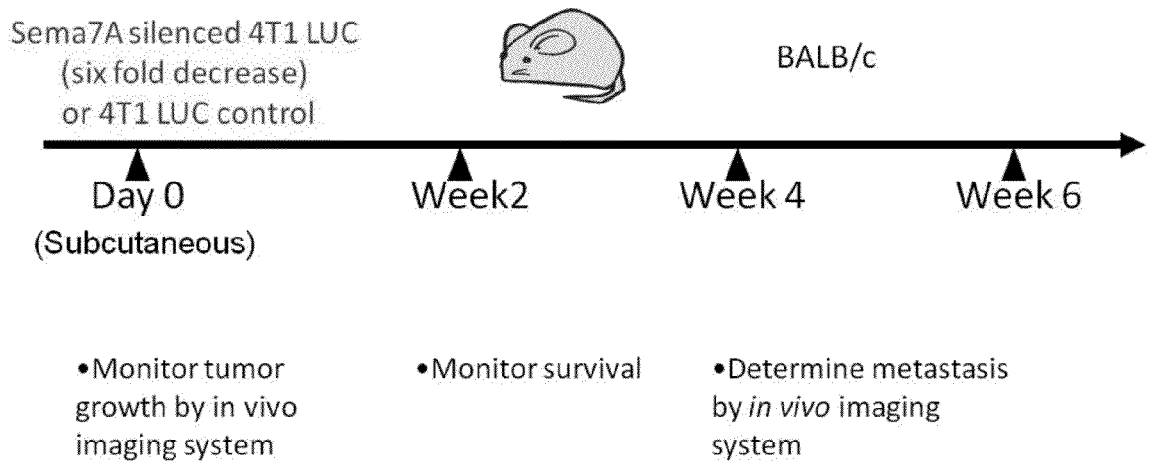
FIG. 2A is a schematic illustrating the protocol for the experimental results shown in FIG. 2B and FIG. 2C.
Figure 2B:
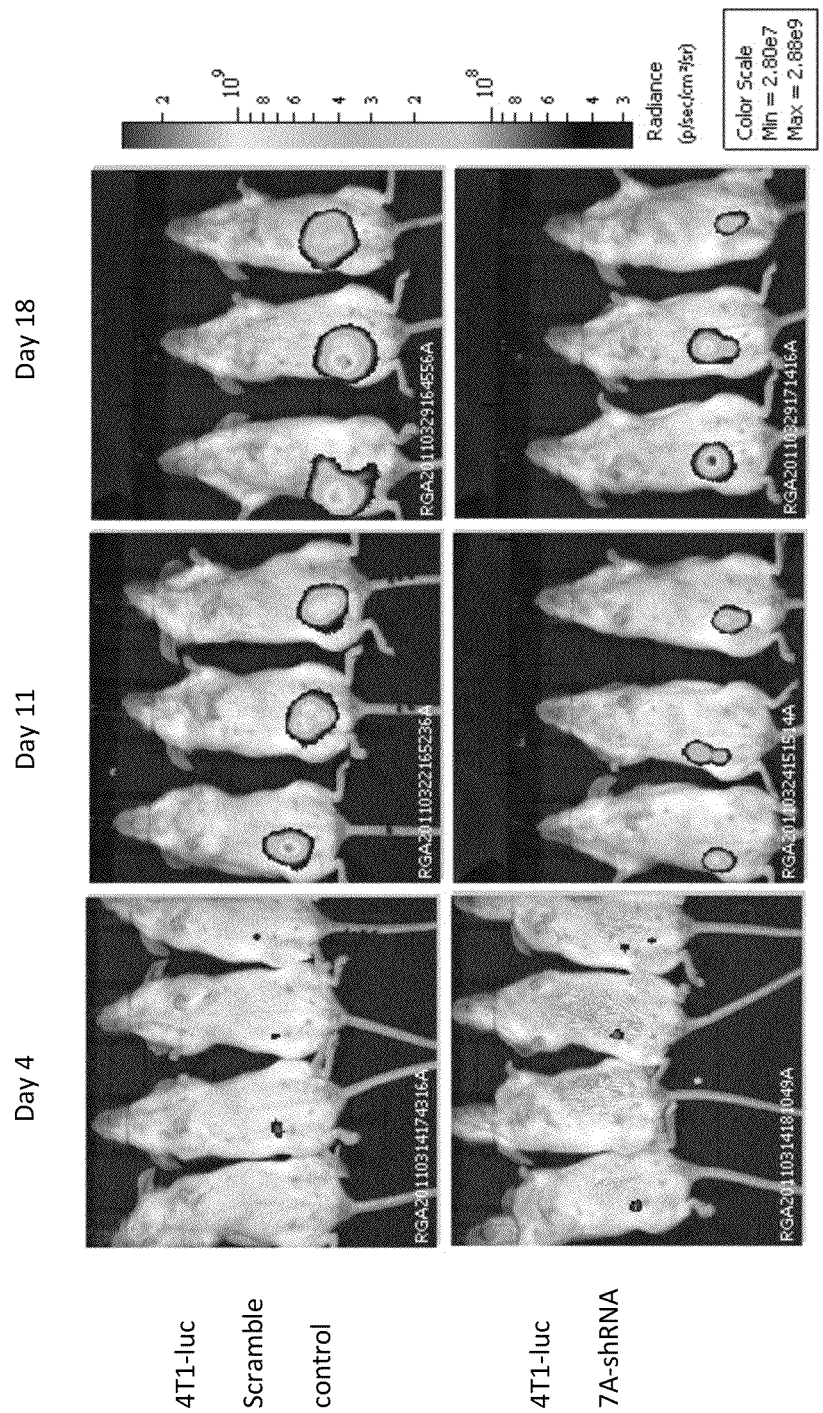
FIG. 2B is a series of photographs of a representative of 14 mice/group at 3 different time points showing that silencing of Sema7A gene in 4T1-luc mammary tumor cells reduces tumor growth.
Figure 2C:
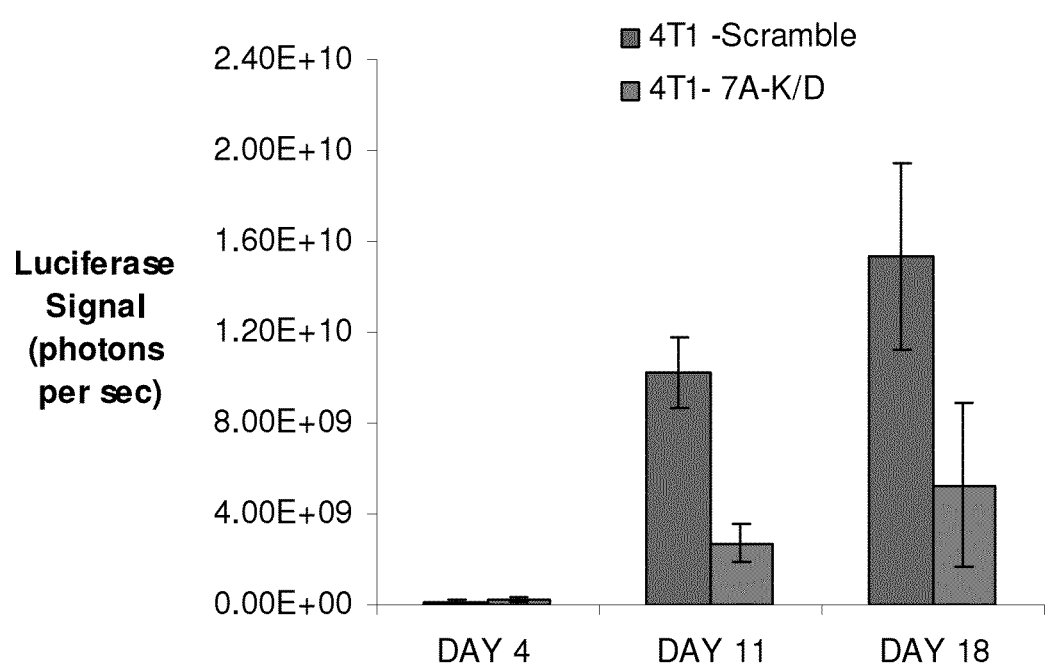
FIG. 2C is a graph showing quantification of tumor-specific bioluminescence signal (photon/cm$^2$/sec) from FIG. 2B.

We also confirmed the expression of Sema7A in the DA-3 cell murine mammary line and within the parental D1-DMBA-3 transferable murine tumor. As expected with a GP1 anchored protein, Sema7A was expressed in the periphery of the tumor cells within the tumor microenvironment. We confirmed the expression of Sema7A in the more aggressive 4T1 murine breast cancer cells and used shRNA to knock down their Sema7A expression. We achieved a 6-fold decrease in Sema7A expression in these cells compared to the scramble control and proceeded to implant these into BALB/c mice. The mice were injected subcutaneously with $1 \times 10^5$ Sema7A silenced 4T1 cells or scramble control in the left lower ventral quadrant. Taking advantage of the 4T1 cell's luciferase tag, we were able to monitor tumor growth using an in vivo bioluminescent imaging system (FIG. 2). At day 11 and 18 it is evident there is a significant decrease in tumor growth in animals bearing the Sema7A silenced 4T1 cells. The tumors could not be imaged past 18 days given the formation necrotic foci that block the emission of the bioluminescent signal.

Figure 3:
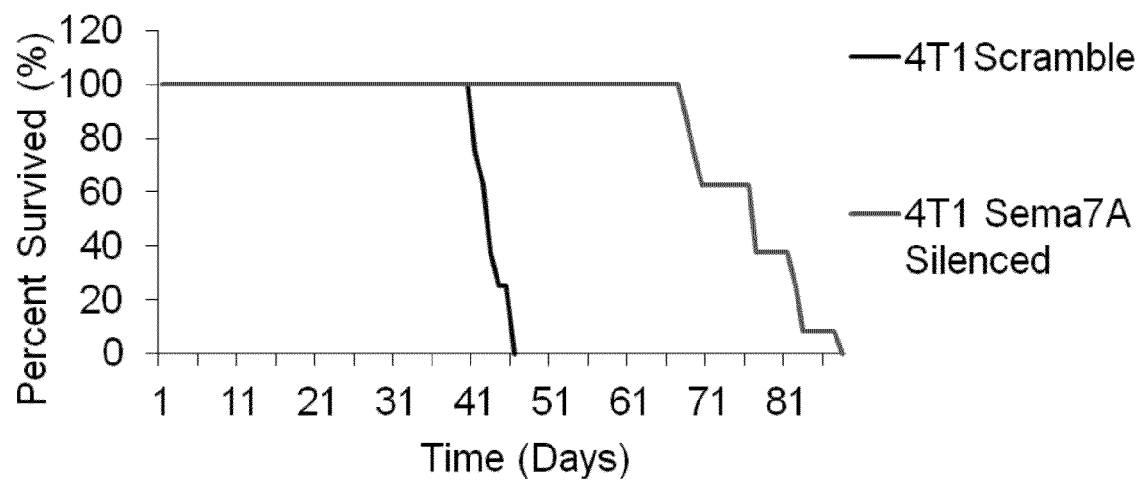
FIG. 3 is Kaplan-Meier survival curve of tumor bearing mice showing increased survival in mice bearing Sema7A shRNA silenced tumors. Graph represents n=14.
Figure 4A:
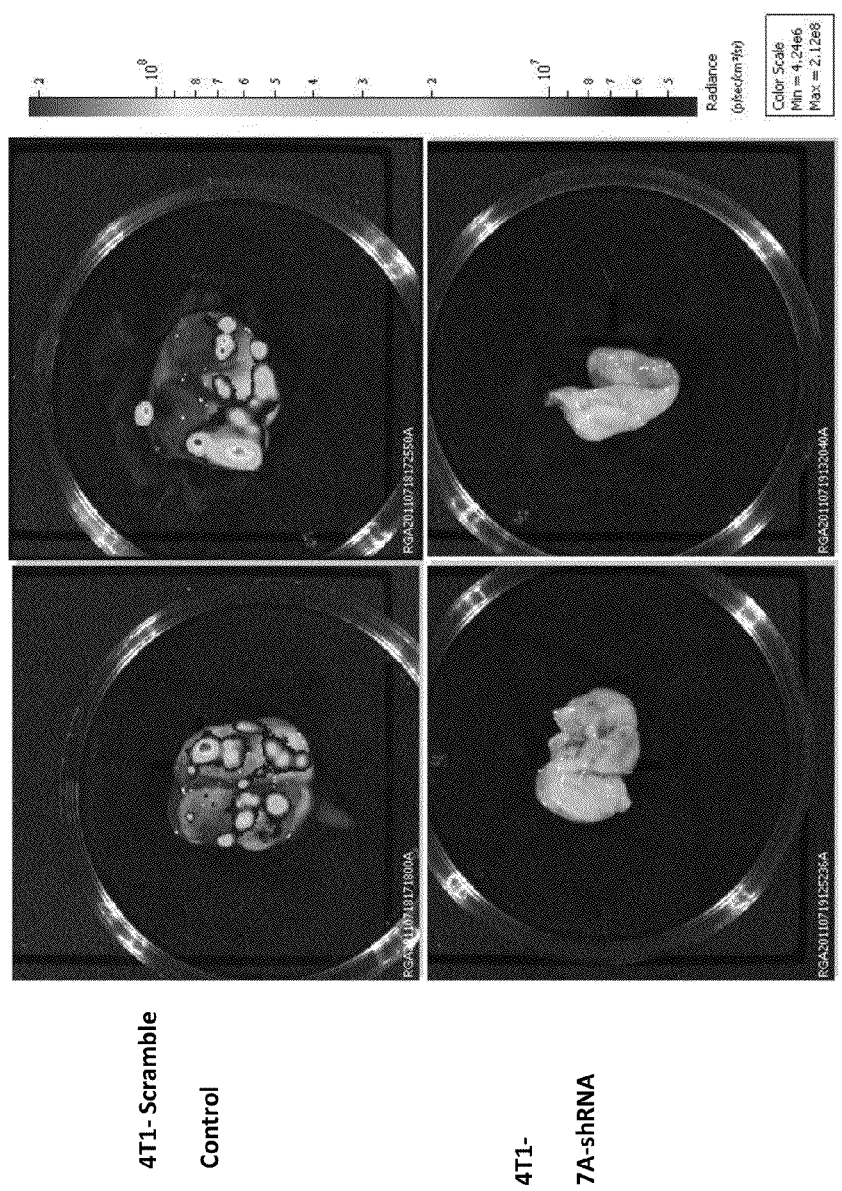
FIG. 4 is a series of photographs and graphs showing decreased lung metastasis in mice bearing Sema7A shRNA-silenced tumors. A. photograph of bioluminescence signal of excised lungs. B. graph showing bioluminescence signal of excised lungs. C. india ink signal showing decreased metastatic foci in lungs of mice receiving Sema7A silenced tumor cells compared to the scramble control. D. counted metastatic foci of lungs from mice receiving Sema7A silenced tumor cells compared to the scramble control.
Figure 4B:
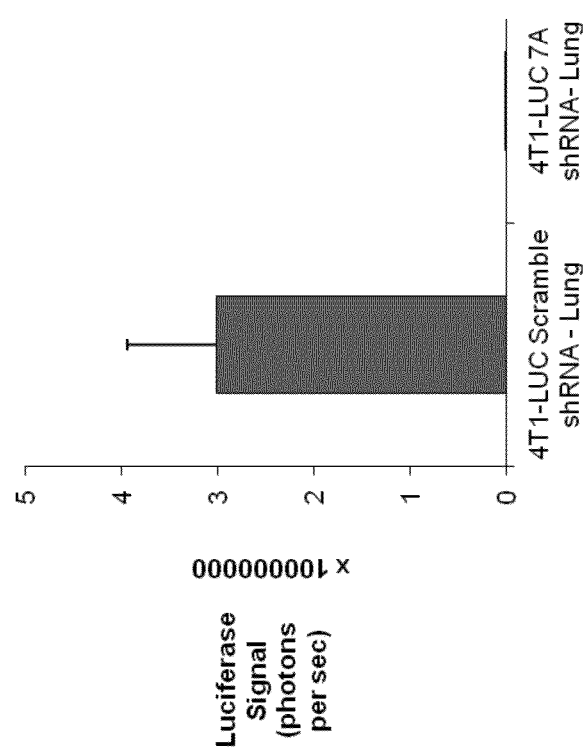
Figure 4C:
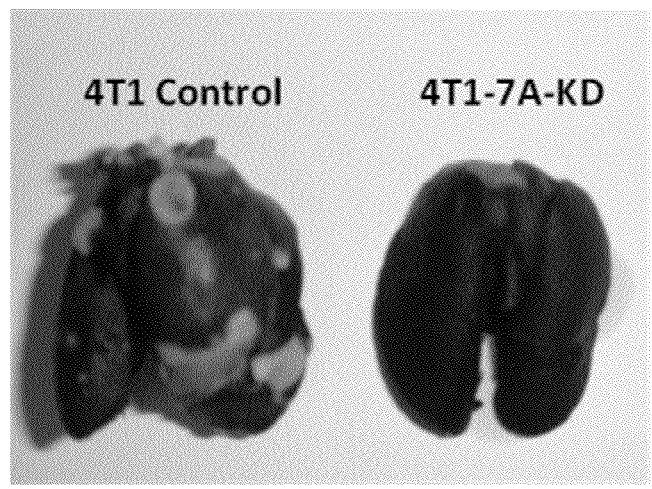
Figure 4D:
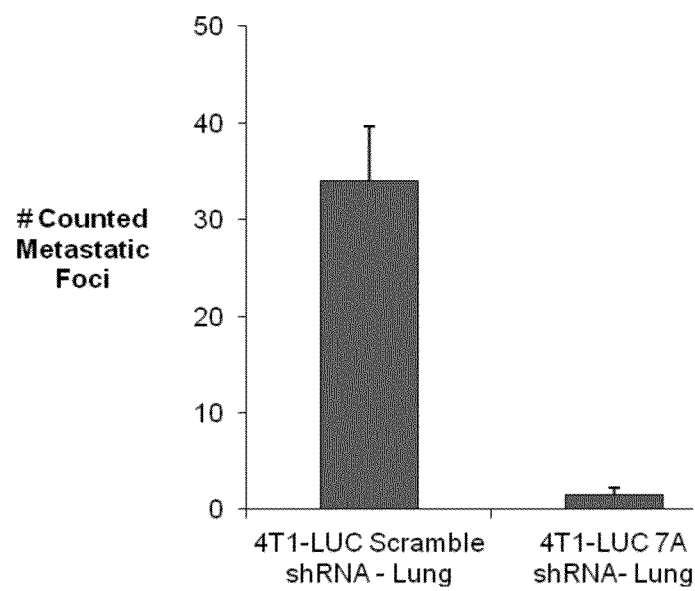

The animal inoculated with the Sema7A silenced cells had improved survival compared to the animals bearing the scramble control 4T1 cells (FIG. 3). FIG. 3 is a Kaplan-Meier survival curve of tumor bearing mice. Graph represents n=14.

We then determined if this increased survival was due to decreased metastasis. As shown in FIGS. 4A-D, we found that Sema7A knock down in 4T1 cells significantly decreased tumor metastasis to the lung. In this experiment, at day 44 post tumor implantation, animals inoculated with Sema7A shRNA silenced (6-fold knock down) 4T1 cells showed decrease metastasis compared to the scramble shRNA control 4T1 cells as determined by India Black staining and by determined by quantification of bioluminescent signal from excised lungs. (n=15).

We compared the gene expression of the Sema7A silenced (6-fold knock down) 4T1-LUC cells to that of the scramble control 4T1-LUC cells by qPCR, using the following gene arrays: Mouse Epithelial to Mesenchymal Transition Array (Table 1), Mouse Tumor Metastasis Array (Table 2), and Mouse Angiogenesis Array (Table 3). In these experiments, RNA was extracted from 4T1-luc scramble control cells and 4T1-luc Sema7A shRNA silenced cells (6-fold silencing of Sema7A). cDNA was made by conventional RT-PCR and then assayed with Qiagen's EMT and Tumo Metastasis qPCR gene array. Silencing Sema7A decreased the expression of mesenchymal markers, MMP3, Osteopontin and vimentin while increasing the expression of epithelial markers desmoplakina and keratin 14 (Table 1). These results highlight the role of Sema7A in epithelial to mesenchymal transition.

TABLE 1

EMT related genes most affected when Sema7A was silenced (6-fold knock down) compared to scramble control
Epithelial to Mesenchymal Transition Array

| Gene | Role | Fold Up- or Down- Regulation Sema7A shRNA/Control Group |
|---|---|---|
| Mmp3 | Mesenchymal Marker | −119.84 |
| Osteopontin | Mesenchymal Marker | −32.11 |
| Vimentin | Mesenchymal Marker | −15.83 |
| Desmoplakin | Epithelial Marker | 4.77 |
| Keratin 14 | Epithelial Marker | 9.68 |

Use of metastasis related gene array to compare the effect of Sema7A gene knockdown revealed that there is a significant decrease in expression of genes associated with metastasis in Sema7A knock-down mammary tumor cells (Table 2). Expression of MMP-13, a matrix metalloproteinase associated with increased invasiveness was downregulated by more than 90-fold when Sema7A gene expression was decreased by 6-fold. Other metastasis associated gene expression including MMP-10, urokinase receptor and TGF-β and its signaling molecule Smad4 also decreased significantly. In contrast, expression of two of the genes that negatively regulate metastasis trP53 and Pten were up-regulated in Sema7A knock-down mammary tumor cells.

TABLE 2

Metastasis related genes most affected when Sema7A was silenced (6-fold knock down) compared to scramble control
Metastasis Related Genes

| Gene | Fold Up- or Down- Regulation Sema7A shRNA/Control Group |
|---|---|
| Mmp13 | −94.09 |
| Mmp10 | −24.35 |
| Urokinase Receptor | −12.87 |
| Transforming growth factor beta 1 | −9.89 |
| Cd44 | −8.09 |
| Smad4 | −3.75 |
| Mmp9 | −3.57 |
| trP53 | 2.23 |
| Pten | 2.29 |

The Sema7A knock down 4T1 cells also showed decreased expression of angiogenesis-related genes (Table 3). The most down-regulated of these genes was CCL-2. This chemokine is not only an angiogenic molecule, but it is also an important immune cell chemoattractant. Therefore Sema7A may also be mediating cell migration indirectly via CCL-2. The inflammatory mediators IL-6 and TNFα were also decreased, consistent with the studies stating that Sema7A is involved in the inflammatory response. To a lesser extent, the VEGF A expression by 4T1 cells was also diminished after Sema7A silencing.

TABLE 3

Angiogenesis related genes most affected when Sema7A was silenced (6-fold knock down) compared to scramble control
Metastasis Related Genes

| Gene | Fold Up- or Down- Regulation Sema7A shRNA/Control Group |
|---|---|
| Chemokine (C-C motif) ligand 2 | −42.15 |
| Placental growth factor | −8.56 |
| Interleukin 6 | −8.33 |
| Tumor necrosis factor | −5.73 |
| Vascular endothelial growth factor A | −2.41 |

Figure 5:
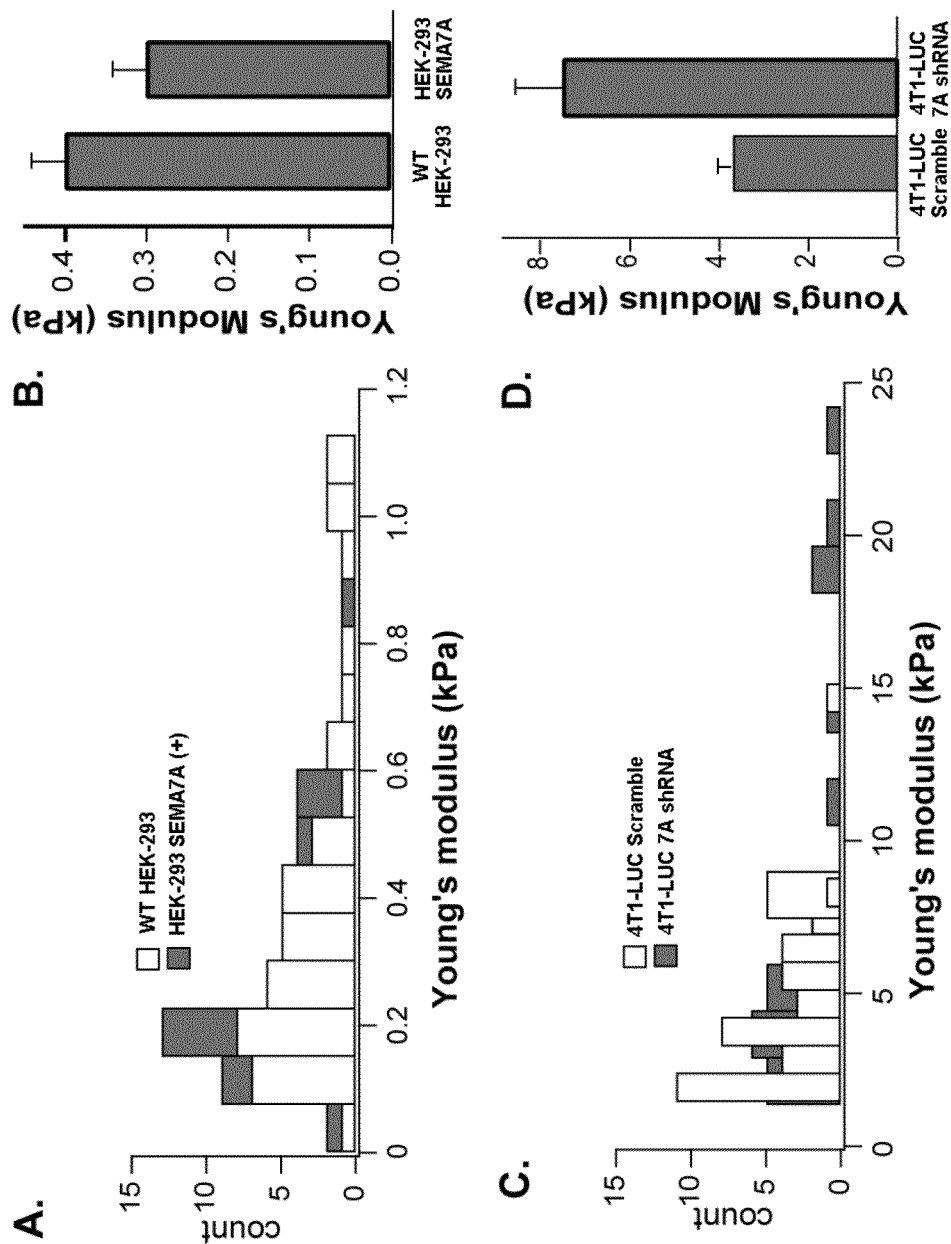
FIG. 5 is a series of graphs showing results from atomic force microscopy study. A. Data distribution of Young's modulus values for Wild-type HEK293(white; n=45) and Sema7A transfected HEK293 cells (blue; n=44). B. Average of Young's modulus values for stiffness measurements from A. C. Data distribution of Young's modulus values for 4T1-LUC scramble shRNA control cells (white; n=35) and 4T1-LUC 6-fold shRNA Sema7A gene knockdown cells (blue; n=29). D. Average of Young's modulus values for stiffness measurements from C. The error in both B and D is the SEM.

Referring to FIG. 5, in these experiments, AFM measurements of cell stiffness were acquired at 37° C. at a constant cantilever reaction rate, applied force and contact time.

We found that Sema7A is up-regulated in the tumor tissues of breast cancer patients but expression is minimal in the adjacent normal tissue. We showed that differential expression of Sema7A in breast cells lines enhances a mesenchymal/stem-like phenotype. We postulate that these changes involve cytoskeletal remodeling as indicated by the altered cell stiffness measured by AFM. Furthermore, implantation of breast tumor cell lines with altered Sema7A expression in BALB/c mice affected tumor growth, metastasis and survival. Cells that were silenced for Sema7A expression showed a decreased mesenchymal profile, had lower metastatic and angiogenic potential.

In conclusion, the following observations were made. Sema7A Sema7A is up-regulated in the tumor tissue of breast cancer patients and more so in the breast cancer stem cells.

Sema7A gene silencing in 4T1 mammary tumor cell results in decreased tumor growth, increased survival and decreased lung metastasis. Gene arrays revealed that Sema7A gene silencing has an effect on genes related to the epithelial to mesenchymal transition and metastasis. Sema7A expression is increased in malignant human breast cancer cells lines displaying a mesenchymal phenotype. TGFb$_1$ up-regulates Sema7A expression in MCF-10A mammary epithelial cells. In the tumor microenvironment Sema7A could contribute to tumor cell migration and tissue remodeling. Sema7A could prove to be a novel therapeutic target to limit tumor growth and metastasis not only for breast cancer but for other solid tumors as well.

Example 2

Research Strategy and Design

Patient Selection Criteria:

Specimens are collected from female breast cancer patients and controls subjects that have tested negative for breast cancer after a mammogram. Breast cancer patients are categorized by stage of disease and grouped according to results of mammography, ultrasound, MRI and percutaneous biopsies. All specimens come from the Lynn Cancer Center in Boca Raton, Fla.

Mouse Studies:

For the in vivo studies BALB/c mice are inoculated with 4T1-luc-2 cells ($0.1 \times 10^6$) or derivatives of this cell line. Using shRNA, the Sema7A gene is knocked down in 4T1-luc-2 cells and denoted as 4T1-luc-7AKD. In addition, 4T1-luc-2 cells are transfected to over-express Sema7A and are denoted as 4T1-luc-7AOE.

To Correlate Sema7A Expression with Disease in Breast Cancer Patients.

Studies have shown that Sema7A is enzymatically cleaved from the membrane of platelets by tumor necrosis factor-α-converting enzyme (TACE, aka ADAM-17). We previously reported that TACE is highly active in breast cancer cell lines and cleaves Sema7A off the tumor cell membranes. It is possible that Sema7A is cleaved from the tumor cells of breast cancer patients and is therefore increased in circulation. In addition to tumor cells, immune cells also express Sema7A. We have found that leukocytes from tumor bearing mice have increased Sema7A compared to normal controls. Tumor-derived factors induce Sema7A expression in immune cells and these may also contribute to circulating levels of Sema7A Our preliminary studies show that Sema7A is up-regulated in the tumor tissue of seven breast cancer patients compared to normal controls, and more so in the cancer stem cells.

Establish Soluble Sema7A Serum Levels in Breast Cancer Patients and Breast Cancer Free Control Subjects.

Towards this Aim, 15 milliliters of peripheral blood are drawn into heparinized tubes from breast cancer patients and normal age-matched controls. Samples are centrifuged and serum is collected for subsequent Sema7A sandwich ELISA (USCN Life Sciences). For these studies, N=40 subjects are needed to obtain data for statistical significance. Statistical analysis is performed by two-way ANOVA. Breast cancer patients are anticipated to have increased serum levels of Sema7A compared to controls.

Determine Sema7A Expression in Peripheral Blood Leukocytes from Breast Cancer Patients and Breast Cancer Free Control Subjects.

Towards this Aim, 5 milliliters of fresh peripheral blood is collected into EDTA coated tubes from breast cancer patients and breast cancer free controls. Within 24 hours, leukocyte RNA is extracted using the QIAamp® RNA Blood Mini kit. The RNA is quantified and 500 ng of RNA is used to produce cDNA. This cDNA is then used to assay Sema7A mRNA levels using SABiocience's qPCR primer array. For these studies, N=40 subjects are needed to obtain data for statistical significance. Statistical analysis is performed by two-way ANOVA. Leukocytes from breast cancer patients are anticipated to have higher Sema7A mRNA expression compared to controls. If necessary, RNA extraction from peripheral blood leukocytes is optimized by pre-separating cells by Ficoll gradient separation. Alternatively, an anti-Sema7A antibody is used to stain the leukocytes and analyze by flow cytometry.

Determine Sema7A Expression in Breast Tumor Tissue, Breast Cancer Stem Cells and Normal Adjacent Tissue of Breast Cancer Patients.

Surgically sectioned breast cancer tissue is obtained from consented patients. The surgeon transects the tumor indicating the normal adjacent tissue from the tumor tissue. From the dissected tissue, an estimated 50 mg of fresh tissue is placed in Celprogen Breast Cancer Stem Cell Complete Growth Media and the rest is submitted for standard pathological analysis (Ki67%, ER+/−, PR+/−, Her2+/−). The fresh tissue is processed within 48 hours and divided into two parts. One half is used to obtain breast cancer stem cells by isolating CD133 positive cells with the Miltenyi cancer stem cells cell separation assay. The other half of the tissue is processed as a heterogeneous population of tumor cells called parental cells. Upon further growth and proliferation of cells from normal adjacent, breast cancer stem cells and parental cells, the cells are processed for gene expression profile and Sema7A expression using SABioscience's qPCR primer assay. Sema7A is correlated with known genes involved in the epithelial to mesenchymal transition (e.g. Vimentin, N-Cadherin). For these studies, N=40 subjects are needed to obtain data for statistical significance. Statistical analysis is performed by student t-test.

Increased Sema7A in tumor tissues and more so in cancer stem cells is anticipated. By expanding the number of patients from seven to forty, statistical significance is established. Cancer stem cells appear in low frequency, and more than 50 mg of tumor tissue may be used to obtain a sufficient number of breast cancer stem cells to assay. If the Miltenyi separation kit is sufficient to obtain a purified population of cancer stem cells, further separation by FACS may be necessary using additional cancer stem cell markers.

To Elucidate the Mechanisms Involved in Sema7A Induction and the Downstream Effects of Sema7A on Metastatic Potential.

Studies in a murine pulmonary fibrosis model found that TGF-β$_1$ induces Sema7A expression via the PI3K/AKT pathway and not through the canonical Smad signaling pathway. We have found that TGF-β$_1$ up-regulates Sema7A in MCF-10A. However, it is still undermined if PI3K/AKT is also responsible for mediating Sema7A over-expression in our breast cancer model. Since Sema7A plays a downstream role in increasing dendricity, cell adhesion and motility in other systems, it is possible for Sema7A to change the phenotype of breast epithelial cells.

Assess which Pathway(s) Play a Role in the TGF-β1 Induction of Sema7A in Breast Cell Lines.

Several breast cell lines of varying degrees of malignancy (MCF10-A, MCF-7, MD-231) are pre-treated with a MAP kinase inhibitor (U0126), a SMAD2/3 inhibitor (SIS3), PI3K/AKT inhibitor (LY294002), DMSO control or Growth media control and then stimulated with TGF-β$_1$. The cells are analyzed for Sema7A by qPCR and western blotting. A dominant-negative mutation is made to the pathway resultant in the most significant decrease of Sema7A expression to confirm that this pathway mediates TGF-$\beta_1$ induction of Sema7A Sema7A induction is expected to be dependent on the PI3K/AKT in the breast cell lines after TGF-$\beta_1$ stimulation. The signaling pathway inhibitors can be toxic to the cells given all these pathways are involved in cell survival. Titration of the concentration of inhibitors may be used to reduce toxicity as well as optimize the pre-treatment time. As an alternative, siRNA targeting of the specific elements of the pathways instead of chemical inhibitors may be used.

Determine if Differential Production of Sema7A Affects the Expression of Epithelial and Mesenchymal Markers, as Well as Metastasis-Related MMPs.

MCF-10A cells characterized by having a benign phenotype are transfected with a plasmid encoding for full length Sema7A to determine if this confers on them a malignant phenotype. In trying to assess cis/trans interactions of Sema7A and its receptors, the phenotype of MCF-10A cells transfected with the full-length, membrane anchored Sema7A is compared to MCF-10-A cells transfected with a plasmid encoding for the truncated, soluble form of Sema7A. To assess the role of $\alpha 1\beta 1$ integrin-Sema7A interaction in promoting malignancy, MCF10-A is transfected with a plasmid encoding wild type Sema7A or Sema7A with a mutated integrin binding domain. The phenotype of the above mentioned modified cells is determined using gene array analysis, focusing on genes involved in epithelial to mesenchymal transition as well metastasis-related MMPs. The loss or gain of mesenchymal markers (Vimentin, MMP-3, MMP-13, MMP-9, Osteopontin, N-Cadherin) and epithelial markers (E-cadherin, desmoplakin, keratin 14) of the modified cells is confirmed by Western blotting. Given that mesenchymal cancer stem cells show the highest expression of Sema7A in the human breast tumor tissue, flow cytometry is used to assess the loss or gain of stem cell markers (CD133, CD44, CD29) upon altering Sema7A expression in the different modified cell lines. Transfecting MCF-10A cells with Sema7A encoding plasmids is expected to induce them to undergo an epithelial to mesenchymal transition. Therefore, they will have increased invasive potential.

Determine if Sema7A Affects the Morphology and Invasive Potential of Breast Epithelial Cells.

The invasive potential of the modified cells and controls described above are determined by their in vitro ability to degrade matrixes and migrate through mesenteric membranes which are representative of the breast basal lamina. Modified cells and controls are also grown in 3D matrigel cultures to determine their increased or decreased ability to form mammospheres and the formation of microtentacles. Changes in morphology and tentacle formation are determined by confocal immunohistochemistry using anti-tubulin and anti-actin antibodies. Changes in the Rho/ROCK and the MAPkinase pathways are also examined by western blotting because these pathways are highly involved in cell migration and cytoskeleton rearrangement. MCF-10A expressing Sema7A is expected to form undifferentiated spheres and have enhanced microtentacle formation.

Statistical Analysis:

To establish statistical significance, a minimum of three independent experiments is analyzed. Statistical analyses include a factorial followed by appropriate post-hoc comparisons (Bonferonni/Dunn or Scheffe tests), and differences are considered statistically significant with values of $p \leq 0.05$.

Assess how Silencing and Over-Expressing Sema7A in Mammary Tumor Cells Affects Tumor Growth and Metastasis In Vivo.

Since Sema7A expression has been shown to affect cell adhesion and motility, the hypothesis that Sema7A may play a role in mammary tumorigenesis and metastasis is tested. Sema7A is known to modulate immune functions, especially affecting the chemotaxis of monocytes and by inducing macrophages to secrete angiogenic and inflammatory mediators. Based on previous published reports of Sema7A as an immune modulator and our finding that Sema7A regulates chemoattractant and angiogenic chemokine CCL-2, modifying Sema7A expression is expected to have an impact on leukocyte infiltration and vascularization.

Determine the In Vivo Effect of Silencing Sema7A in 4T1 Cells on Tumorigenesis.

Luciferase transfected breast cancer 4T1 cells (Sema7A constitutively expressing & Sema7A silenced) are implanted into mammary fat pads of BALB/c mice. Tumor growth and metastasis is monitored by physical measurements and by in vivo bioluminescent imaging using the IVIS Lumina Imaging System. Sema7A silencing in the 4T1 cells is expected to reduce tumor growth and metastasis.

Determine the In Vivo Effect of Over-Expressing Sema7A in 4T1 Cells on Tumorigenesis.

Towards this goal, 4T1 tumor cells transfected with Sema7A plasmid are injected into mammary fat pads of BALB/c mice. Tumor growth and metastasis are monitored by physical measurements and by in vivo bioluminescent imaging using the IVIS Lumina Imaging System. Sema7A over-expression in the 4T1 cells is expected to enhance tumor growth and metastasis. As an alternative, exogenous Sema7A is administered before and after tumor implantation to enhance Sema7A effects on tumorigenesis.

Assess if Tumor Derived Sema7A Affects Leukocyte Infiltration, Neovascularization and Cell Survival/Proliferation.

Transplanted tumors are harvested, snap frozen, sectioned and Hematoxylin-Eosin stained to determine infiltrates and vascularization. To determine leukocyte infiltration in tumors, sections are double labeled with an anti-CD45 antibody. To further assess neovasculariztion, tumor sections are labeled with anti-CD31 antibody and imaged by confocal microscopy. Reduced expression of Sema7A is expected to decrease leukocyte infiltration and angiogenesis; over-expression of Sema7A is expected to have the converse effect. Paraffin embedding of the tumors may be used to obtain thinner tumor sections for immunohistochemical staining. An alternative way to assess tumor infiltrates employs flow cytometry analysis to characterize the heterogeneous tumor cell population.

Statistical Analysis:

To establish statistical significance, a minimum of n=10 animals per group are analyzed. Statistical analyses include a factorial followed by appropriate post-hoc comparisons (Bonferonni/Dunn or Scheffe tests), and differences are considered statistically significant with values of $p \leq 0.05$.

OTHER EMBODIMENTS

All genes, gene names, and gene products disclosed herein are intended to correspond to homologs from any species for which the kits, assays, and methods disclosed herein are applicable. Thus, the terms include, but are not limited to, genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In preferred embodiments, the genes or nucleic acid sequences are human.

Any improvement may be made in part or all of the kits, assays, and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:

1. A method of inhibiting growth of breast cancer cells in a subject, comprising administering to the subject a composition comprising a therapeutically effective amount of a Sema7A inhibitor that is an RNA molecule that reduces or prevents expression of Sema7A for inhibiting growth of breast cancer cells in the subject.

2. The method of claim 1, wherein administration of the composition to the subject results in death of breast cancer stem cells in the subject.

3. The method of claim 1, wherein administration of the composition to the subject decreases or prevents metastasis of the breast cancer cells.

4. The method of claim 1, wherein the Sema7A inhibitor is Sema7A-specific siRNA.

* * * * *